US006221387B1

(12) United States Patent
Hauton et al.

(10) Patent No.: US 6,221,387 B1
(45) Date of Patent: Apr. 24, 2001

(54) GELIFIED MICROSPHERES, THEIR METHOD OF PREPARATION AND THEIR APPLICATIONS

(75) Inventors: Jacques Hauton, Marseilles; Jean-Pierre Salles, Eguilles, both of (FR)

(73) Assignee: Lipogel, Allauch Cedex (FR)

( * ) Notice: Subject to any disclaimer, the term of this patent is extended or adjusted under 35 U.S.C. 154(b) by 0 days.

(21) Appl. No.: 09/300,435

(22) Filed: Apr. 28, 1999

Related U.S. Application Data

(62) Division of application No. 08/722,173, filed as application No. PCT/FR95/00473 on Apr. 12, 1995, now Pat. No. 5,945,120.

(30) Foreign Application Priority Data

Apr. 12, 1994 (FR) .................................................. 94-04294

(51) Int. Cl.[7] .............................. A61K 9/127; A61K 9/16
(52) U.S. Cl. ..................... 424/450; 424/1.21; 424/9.321; 424/9.51; 424/417; 424/943; 424/489; 424/490; 424/491; 424/492; 424/493; 424/497; 264/4.1; 264/4.3; 264/4.6; 428/402.2

(58) Field of Search .................... 424/450, 489–493, 424/497, 1.21, 9.321, 9.51, 417, 94.3; 264/4.1, 4.3, 4.6; 428/402; 935/54

(56) References Cited

U.S. PATENT DOCUMENTS

| 4,708,861 | | 11/1987 | Popescu et al. ........................ 424/1.1 |
| 4,740,375 | * | 4/1988 | Geho .................................... 426/450 |
| 4,839,111 | * | 6/1989 | Huang ................................... 264/4.6 |
| 5,008,109 | | 4/1991 | Tin et al. .............................. 424/422 |
| 5,464,629 | * | 11/1995 | Monshipouri ......................... 426/450 |
| 5,626,870 | | 5/1997 | Monshipouri et al. .............. 424/450 |

* cited by examiner

Primary Examiner—Gollamudi S. Kishore
(74) Attorney, Agent, or Firm—Oblon, Spivak, McClelland, Maier & Neustadt, P.C.

(57) ABSTRACT

Microspheres comprising a gelified polar core which is optionally surrounded by concentric and alternating superimposed n lipidic bilayers or n aqueous liquid layers and n gelified polar layers, n being an integer. The microspheres of the invention are obtainable by delipidation of liposomes designated as liposomes having a gelified polar core, of the type comprising at least one outer lipidic bilayer and at least one inner polar aqueous phase containing a gelified substance.

21 Claims, 5 Drawing Sheets

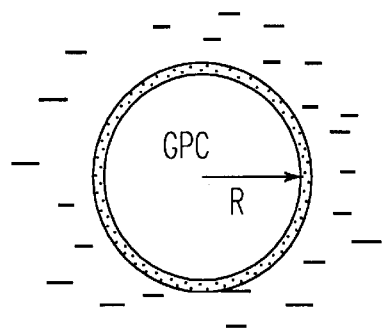
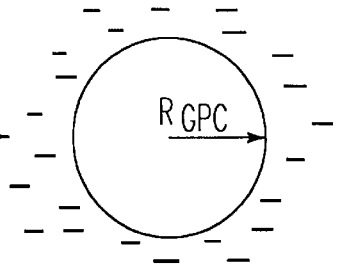
*FIG. 1A*  *FIG. 1B*
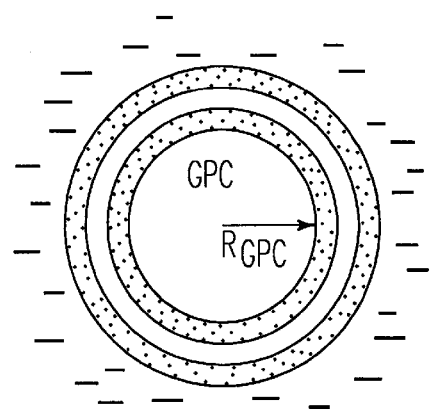
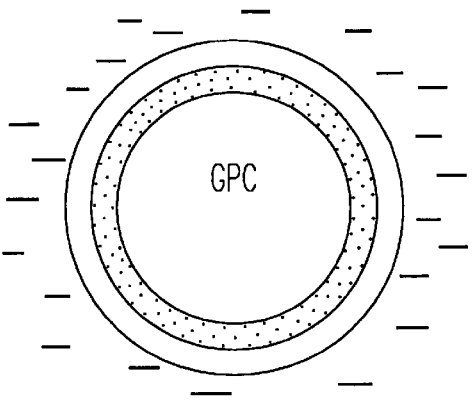
*FIG. 2A*  *FIG. 2B*
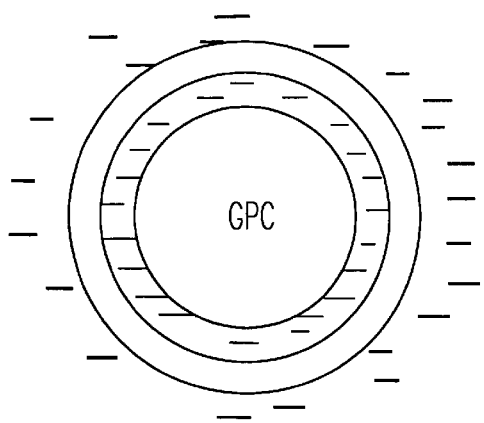
*FIG. 2C*

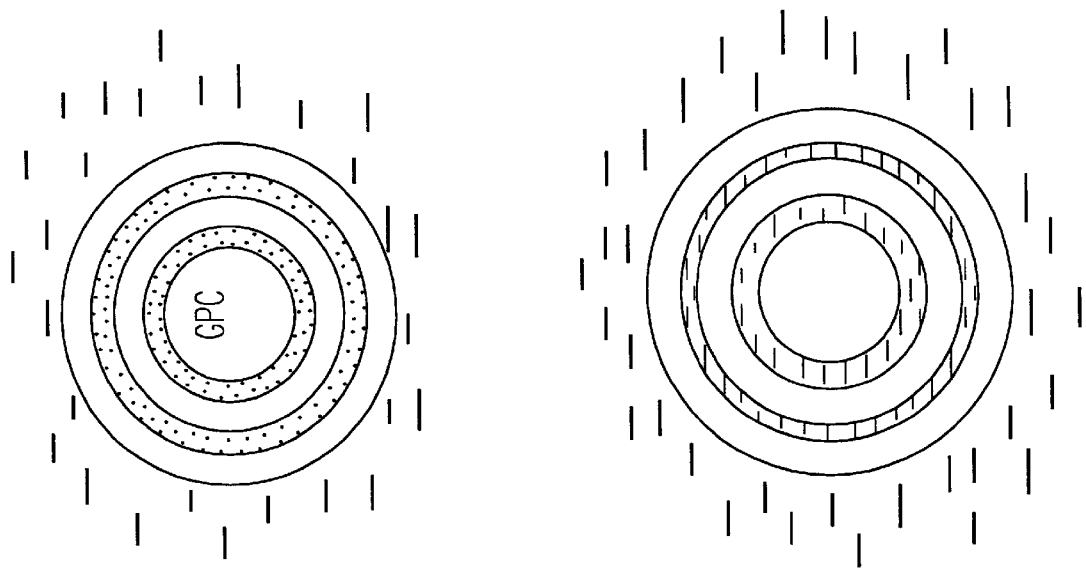
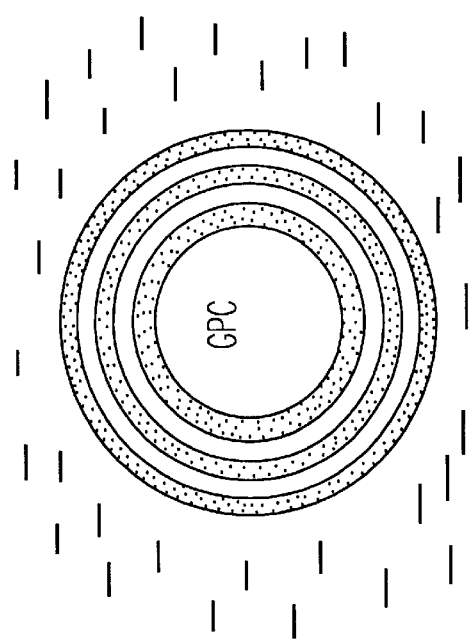
FIG. 3

GELIFIED MICROSPHERES, THEIR METHOD OF PREPARATION AND THEIR APPLICATIONS

This application is a Division of application Ser. No. 08/722,173 filed on Dec. 13, 1996, now U.S. Pat. No. 5,945,120 which was filed as International Application No. PCT/FR95/00473 filed Apr. 12, 1995.

The present invention relates to gelified microspheres, to their method of preparation and to their applications.

Microspheres, which are particles of spherical shape, the size of which ranges, generally, between 1 and 1250 µm, are composed of a support material containing the encapsulated substance and are of particular advantage, either when it is desirable to administer a medicament in a form which makes possible the controlled release of the active component over a certain period, in order to provide for a prolonged pharmacological effect, or when it is necessary to protect the said active component from premature degradation in the digestive tract.

Depending on the structure of the support material, two types of microcapsules are distinguished:

microcapsules of reservoir type, in which the support material is a solid envelope of variable thickness containing the substance to be encapsulated, microcapsules of matrix type, also known as microspheres, in which the support material is a continuous network in which the substance to be encapsulated is dispersed.

Within the meaning of the present invention, the term microcapsule or microsphere comprises only microcapsules or microspheres of matrix type.

Many substances can be encapsulated: it can relate to chemicals, such as medicaments, or alternatively to macromolecules, such as enzymes, and also to living cells.

Microspheres are used in many fields, such as pharmaceuticals, the biotechnology industry, cosmetology, the agri-foodstuffs industry, the paper-manufacturing industry, and the like.

A number of methods for the preparation of microcapsules have been described; mention may in particular be made of:

the phase-separation method, described in particular in U.S. Pat. No. 4,675,189 and Application EP 52,510, which describes microcapsules prepared by a phase-separation technique using a coacervation agent, such as mineral oils or vegetable oils.

However, the microcapsules prepared by this method and by other analogous methods have the disadvantage of forming clusters (inter-adhesion of particles) during the preparation of the said microcapsules.

the solvent-evaporation method, described in particular in U.S. Pat. No. 4,479,911, Application EP 301,969 and Application EP 145,240; this method comprises the separate formation
of an organic phase by dissolution of a suitable polymer in a volatile water-immiscible solvent and
of an aqueous phase containing the advantageous active principle, the addition of the aqueous phase to the organic phase, the mixing of the two phases with agitation and/or in the presence of an emulsifying agent and then the evaporation of the solvent, generally with agitation and at room temperature, in order to obtain the desired microcapsules.

Application EP 145,240 more particularly describes microcapsules produced by preparing a W/O emulsion (primary emulsion) comprising an inner aqueous layer containing a hydrophilic substance and a so-called medicament-retention substance (natural or synthetic mucilage or high-moleculer-weight compounds and more particularly gelatin) and an oily layer containing a polymer, preferably a polylactic acid or a copolymer of lactic acid and of glycolic acid or their mixtures, in a water-immiscible solvent such as dichloromethane, by then thickening or solidifying the said inner aqueous layer so as to obtain a viscosity greater than 5,000 centipoises, by then preparing a secondary W/O/W emulsion in the presence of a suitable surface-active agent and, finally, by subjecting the emulsion thus obtained to evaporation of the solvent. The process described in this Application makes it possible to obtain microcapsules with a diameter of between 0.5 and 400 µm.

However, these microcapsules or microspheres of the prior art have the major disadvantage of having diameters of the order of a µm or more (1–1250 µm); now, there exist many applications for which it is necessary and/or particularly advantageous to be able to have available particles having a significantly smaller diameter, in particular of the order of an nm or more, for example between 20 and 600 nm.

The Applicants have consequently devoted themselves to the goal of developing gelified microspheres, the diameter of which can be controlled and can reach, if necessary, 20 nm.

The subject of the present invention is microspheres, characterized in that they comprise a gelified polar core (GPC) around which are superimposed, concentrically and alternately, n lipid bilayers or a aqueous layers in the liquid state and n gelified polar layers, n being an integer, and in that they are capable of being obtained by delipidation of liposomes, called lipogelosomes® (trademark applied for on behalf of the company Lipogel and denoting liposomes with a gelified polar core), of the type containing at least one outer lipid bilayer and at least one inner polar aqueous phase containing a gelified substance.

Such microspheres advantageously:

exhibit a controllable diameter, preferably of between 20 and 600 nm, are stable, can enclose water-soluble active substances, allow the preparation of both immediate-release or delayed-release forms, depending on the melting point of the gelified substance, can be used as the basis for the attachment of ligands, of substances which are poorly recognized by the reticuloendothelial system (stealthy microspheres) or of electrically-charged compounds (electrical targeting in electrotherapy), and are capable of being rendered stealthy (non-recognition by the reticuloendothelial system) when they exhibit a diameter of the order of 20–40 nm.

In accordance with the invention, the gelifiable substance is selected from polymerizable or non-polymerizable gelifiable compounds, such as polysaccharides, polypeptides or polyacrylamides.

The non-polymerizable gelifiable substance is preferably selected from gelatin, agarose or carragheenins and the polymerizable gelifiable substance is selected from polyacrylamide gels.

Such liposomes with a gelified polar core or lipogelosomes are described in particular in Patent EP 0,393,049, in which it is specified that they are composed of a bilayer interfacial phase, in the case of unilamellar lipogelosomes, or of a plurality of concentrically superimposed bilayer interfacial phases, in the case of multilamellar lipogelosomes, and of a gelified encapsulated inner polar aqueous phase.

This patent describes, in particular, the method for obtaining such unilamellar or multilamellar lipogelosomes: the gelified encapsulated aqueous phase results from the initial liquid aqueous phase, in which the said lipogelosomes are prepared, by conversion of the said aqueous phase into a gel, due to the presence, in the said aqueous phase, of one or a number of polymerizable or non-polymerizable gelifiable compounds; the non-encapsulated aqueous phase can, in addition, be rendered non-gelifiable by physical, chemical or enzymatic action.

The bilayer interfacial phase or phases are composed, for example, of class-4 lipids (phospholipids), optionally in combination with class-2 lipids and class-3 lipids (free cholesterol) and/or class-5 lipids.

This classification of the lipids, proposed by Professor Hauton et al., based on the partition coefficients $K_D$ between a polar aqueous phase and a monolayer or bilayer interfacial phase and $K_C$ between an interfacial phase and a hydrophobic or non-polar phase, will be used (Hauton and Lafont, Biochimie, 1987, 69, 177–204); it is also described in the abovementioned Patent EP 393,049.

Such lipogelosomes (LGS) are generally classified, according to the number of bilayers:

as small unilamellar lipogelosomes (SULGS) and as large unilamellar lipogelosomes (LULGS) and as multilamellar lipogelosomes (MLGS).

In accordance with the invention, the stage of delipidation of the said lipogelosomes can be carried out in a number of ways and can result in gelified microspheres of controlled diameter:

surface deliDidation of unilamellar or multilamellar limoaelosomes by:

(1) extraction of the surface lipid bilayer of the said unilamellar or multilamellar lipogelosomes by a water-immiscible organic solvent or a mixture of water-immiscible organic solvents;

(2) two-phase partition of the organic phase and of the aqueous phase; and (3) separation of the aqueous phase containing the surface-delipidated gelified microspheres (removal of the outermost bilayer).

In the case of the delipidation of unilamellar lipogelosomes (removal of the sole lipid bilayer), gelified microspheres in accordance with the invention, also called gelosomes® (GS) (trademark applied for on behalf of the company Lipogel) (small homogeneous gelosomes (SHGS); large homogeneous gelosomes (LHGS)) or polymerisomes® (trademark applied for on behalf of the company Lipogel and also denoting gelified microspheres in accordance with the invention) are obtained which are homogeneous, that is to say which do not contain any lipid bilayer, and thus composed of homogeneous gelified aqueous microspheres corresponding to the abovementioned polymerized or non-polymerized gelified polar core (GPC).

In the case of the surface delipidation of multilamellar lipogelosomes (removal of the outermost lipid bilayer), structures are obtained, called hybrid multilayered gelosomes (GS) (hybrid MGS=hybrid multilayered gelosomes) or hybrid multilayered polymerisomes, which are hybrids between liposomes (LGS) and gelosomes (GS) and which are composed of a polymerized or non-polymerized gelified polar core (GPC) on which are concentrically superimposed lipid bilayers separated by polymerized or non-polymerized gelified aqueous layers, the outermost layer being a polymerized or non-polymerized gelified aqueous layer.

Such microspheres in accordance with the invention in fact represent:

unilamellar LGSs, when the non-delipidated starting LGSs, which were used for their preparation, were bilamellar, or multilamellar LGSs, when the non-delipidated starting LGSs, which were used for their preparation, were multilamellar;

these microspheres are surrounded by a polymerized or non-polymerized aqueous surface layer (Table I and FIGS. 2 and 3).

The water-immiscible organic solvent is in particular, and non-limitingly, heptane.

b) comlete delimidation of unilamellar or multilamellar liposomes by:

(1) lipid extraction of unilamellar or multilamellar lipogelosomes by a water-miscible or partially water-miscible organic solvent or a mixture of water-miscible or partially water-miscible organic solvents;

(2) two-phase partition of the organic phase and of the aqueous phase;

(3) separation of the organic solvent or solvents from the aqueous phase; and (4) separation of the gelified and completely delipidated microspheres.

In accordance with the invention, when the stage (1) is carried out using a water-miscible organic phase, a non-polar organic solvent is added prior to the stage (2), thus making possible two-phase partition.

In the case of the complete delipidation of unilamellar lipogelosomes (removal of the sole lipid bilayer), homogeneous gelosomes (GS) or homogeneous polymerisomes, as defined above, are obtained.

In the case of the complete delipidation of bilamellar lipogelosomes, a polymerized or non-polymerized gelified polar core (GPC), surrounded by an aqueous layer in the liquid state and by a single polymerized or non-polymerized aqueous surface layer in the gelified state, is obtained.

In the case of the complete delipidation of multilamellar lipogelosomes, multilayered gelosomes (GS) (MGS= multilayered gelosomes) or multilayered polymerisomes are obtained which are composed of a polymerized or non-polymerized gelified polar core (GPC) on which are concentrically superimposed polymerized or non-polymerized gelified aqueous layers separated from one another by aqueous layers in the liquid state.

The organic solvent is advantageously, but non-limitingly, n-butanol.

Another subject of the present invention is a method for the preparation of microspheres in accordance with the invention, comprising a gelified polar core (GPC=gelified polar core) around which are optionally superimposed, concentrically and alternately, n lipid bilayers or n aqueous layers in the liquid state and a gelified polar layers, a being an integer, which method is characterized in that it comprises:

(a) the preparation of liposomes, called lipogelosomes, of the type containing n+1 lipid bilayers, including an outer lipid bilayer, and at least one inner polar aqueous phase containing a gelified substance, and (b) the delipidation-of the said lipogelosomes.

The stage (a) is described in Patent EP 0,393,049.

According to an advantageous embodiment of the said method, prior to the delipidation stage, the lipogelosomes are selected according to their diameter, preferably by ultrasonication.

According to another advantageous embodiment of the said method, prior to the delipidation stage, the non-encapsulated substances are removed, preferably by tangential ultrafiltration.

A concentrate of lipogelosomes in the ultrafiltration retentate is then obtained; the delipidation stage is then carried out in the said ultrafiltration retentate.

According to another advantageous embodiment of the said method, the delipidation stage (b) comprises, for surface delipidation:

(1) the extraction of the surface lipid bilayer of the said unilamellar or multilamellar lipogelosomes by a water-immiscible organic solvent or a mixture of water-immiscible organic solvents;

(2) the two-phase partition of the organic phase and of the aqueous phase; and (3) the separation of the aqueous phase containing the surface-delipidated gelified microspheres, as defined above.

According to yet another advantageous embodiment of the said method, the delipidation stage (b) comprises, for complete delipidation:

(1) the lipid extraction of unilamellar or multilamellar lipogelosomes by a water-miscible or partially water-miscible organic solvent or a mixture of water-miscible or partially water-miscible organic solvents;

(2) the two-phase partition of the organic phase and of the aqueous phase;

(3) the removal of the organic solvent from the aqueous phase; and (4) the separation of the gelified and completely delipidated microspheres, as defined above.

In addition to the preceeding arrangements, the invention also comprises other arrangements which will emerge from the following description, which refers to implementational examples of the method which is the subject of the present invention and to the appended drawings in which:

FIG. 1 illustrates a gelified microsphere obtained by delipidation of a unilamellar lipogelosome;

FIG. 2 illustrates a gelified microsphere obtained by surface or complete delipidation of a bilamellar lipogelosome;

FIG. 3 illustrates a gelif ied microsphere obtained by surface or complete delipidation of a multilamellar lipogelosome;

Figure 4:
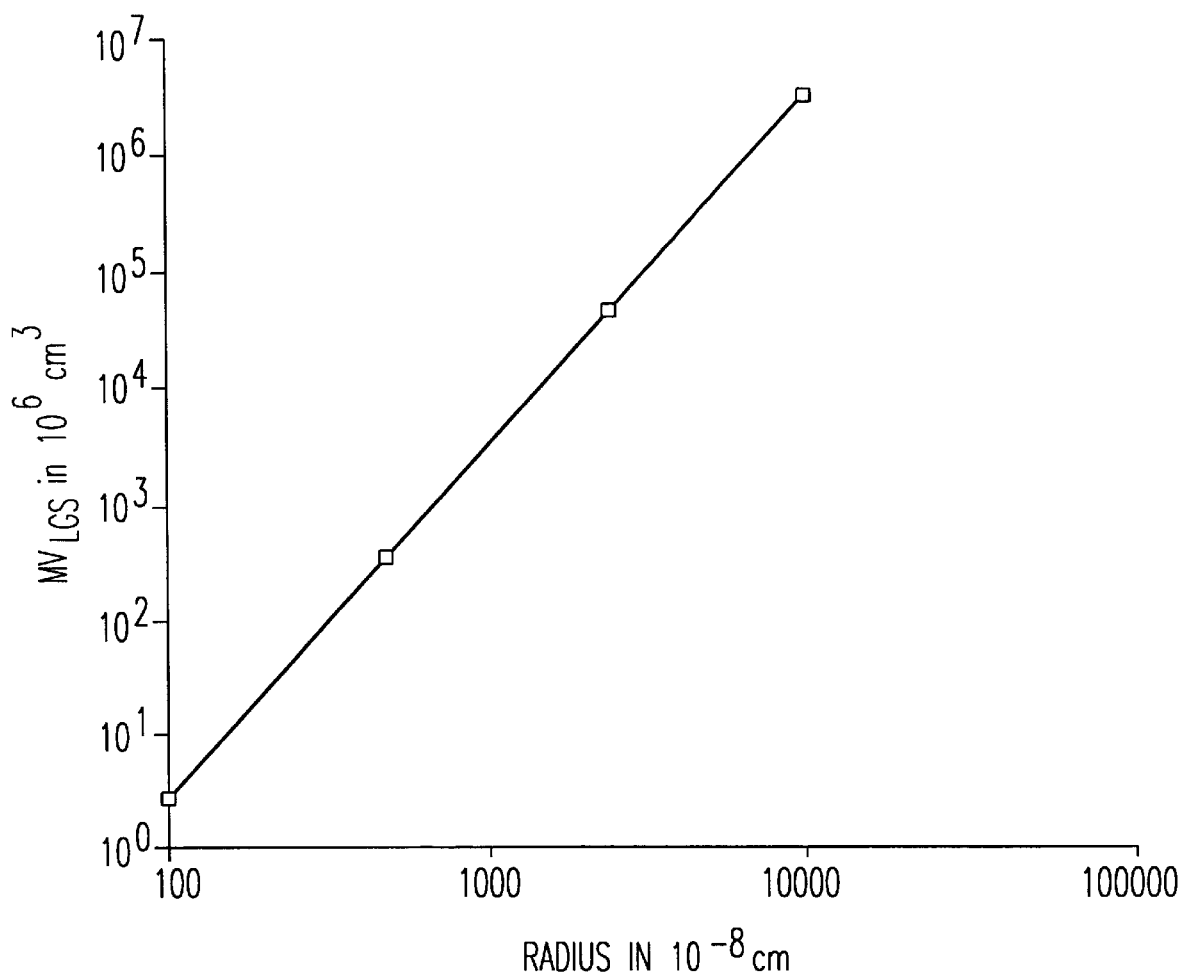
FIG. 4 illustrates the variations in the molar volumes of unilamellar lipogelosomes as a function of the radius R (log/log coordinates)

However, it should be clearly understood that these examples are given solely by way of illustration of the subject of the invention, of which they do not in any way constitute a limitation.

The different types of gelified microspheres in accordance with the invention are illustrated in Table I below and in FIGS. 1 to 3.

TABLE I

| | | Surface delipidation | Complete delipidation |
|---|---|---|---|
| Unilamellar LGSs (SULGS and LULGS) | Non-polymerized GPC | Homogeneous gelosomes (SHGS and LHGS) (FIG. 1) | Homogeneous gelosomes (SHGS and LHGS) (FIG. 1) |
| | Polymerized GPC | Homogenous polymerisomes (FIG. 1) | Homogenous polymerisomes (FIG. 1) |
| Multi-lamellar LGSs (MLGS) | Non-polymerized GPC | Hybrid multi-layered gelosomes: GPC + concentric lipid bilayers by gelified aqueous layers (FIGS. 2 and 3) | Multilayered gelosomes: GPC + concentric separated gelified aqueous layers separated by aqueous layers in the liquid state (FIGS. 2 and 3) |
| | Polymerized GPC | Hybrid multi-layered polymer-isomes: GPC + concentric lipid bilayers separated by gelified aqueous layers (FIGS. 2 and 3) | Multilayered polymer-isomes: GPC + concentric gelified aqueous layers by aqueous layers in the liquid state (FIGS. 2 and 3) |

The polymerized or non-polymerized gelified microspheres obtained by surface or complete delipidation of a unilamellar lipogelosome are illustrated in FIG. 1.

The unilamellar lipogelosomes (SULGS and LULGS) comprise a polymerized or non-polymerized gelified polar core (GPC) (represented in white) with a radius $R_{GPC}$ and a phospholipid bilayer (represented in black) with a thickness $h=10^{-8}$ cm; the radius of the said unilamellar lipogelosomes is $R=R_{GPC}-h$.

By delipidation of the unilamellar lipogelosome, a homogeneous gelosome (SHGS and LHGS), if the gelified polar core is non-polymerized, or a homogeneous polymerisome, if the gelified polar core is polymerized, is obtained, as specified above.

The radius of the polymerized or non-polymerized gelified microsphere in accordance with the invention is equal to $R_{GPC}$.

The liquid aqueous phase surrounding the LGSs and the microspheres is represented by a series of dashes (shading).

The polymerized or non-polymerized gelified microspheres obtained by surface or complete delipidation of a bilamellar lipogelosome are illustrated in FIG. 2.

FIG. 2A represents a bilamellar lipogelosome comprising a polymerized or non-polymerized gelified polar core (GPC) (represented in white) with a radius $R_{GPC}$ and two lipid bilayers (represented in black) with a thickness $h=10^{-8}$ cm separated by a gelified aqueous layer with a thickness H; the radius of the said bilamellar lipogelosomes (LGS) $R_{LGS}= R_{LGS}+2h+H$ (1).

FIG. 2B represents the hybrid multilayered gelosomes or polymerisomes obtained by surface delipidation of the said bilamellar LGSs: as only the surface lipid bilayer is extracted, microspheres are obtained which comprise a polymerized or non-polymerized gelified polar core surrounded by a lipid bilayer and then by a polymerized or non-polymerized gelified surface aqueous layer with a thickness H.

The radius of these microspheres in accordance with the invention is $R=R_{GPC}+h+H$ (2).

FIG. 2C represents the multilayered gelosomes or polymerisomes obtained by complete delipidation of the said bilamellar LGSs: as both lipid bilayers are extracted, a non-homogeneous gelosome or polymerisome is obtained composed of a polymerized or non-polymerized gelified polar core (GPC), an aqueous layer in the liquid state with a thickness h and finally a polymerized or non-polymerized gelified surface aqueous layer with a thickness H; the radius of these microspheres is $R=R_{GPC}+h+H$.

FIG. 3 represents the multilayered gelosomes or polymerisomes obtained by surface delipidation or complete delipidation of multilayered lipogelosomes (MLGS).

These MLGSs comprise a polymerized or non-polymerized gelified polar core (GPC) (represented in white) with a radius $R_{GPC}$ and n lipid bilayers (represented in black), with n=3, the thickness of each bilayer being $h=10^{-8}$ cm; the radius of the said multilamellar lipogelosomes $R_{LGS}=R_{GPC}+nh+(n-1)H$ (3) is, when n=3, equal to $R_{GPC}+3h+2H$ (4).

By surface delipidation of the said trilamellar LGSs, hybrid multilayered gelosomes or polymerisomes are obtained comprising a polymerized or non-polymerized gelified polar core (GPC), a lipid bilayer, then a first gelified aqueous layer, a second lipid layer and then, at the surface, a second polymerized or non-polymerized gelified aqueous layer.

The radius of such microspheres in accordance with the invention is $R=R_{GPC}+2h+2H$ (5).

By complete delipidation of the said trilamellar LGSs, multilayered gelosomes or polymerisomes are obtained comprising a polymerized or non-polymerized gelified polar core (GPC), a first aqueous layer in the liquid state (represented as shaded), a first gelified aqueous layer, a second aqueous layer in the liquid state and then, at the surface, a second polymerized or non-polymerized gelified aqueous layer.

The radius of such microspheres in accordance with the invention is $R=R_{GPC}+2h+2H$.

EXAMPLE 1

Determination of the physical parameters of the lipogelosomes (LGS) and of the microspheres in accordance with the invention (surface-delipidated or completely delipidated): assessment of the control of the diameter of the microspheres.

A necessary condition for obtaining a standardized method for calculating the physical parameters of well-defined type of spherical particle is to strictly observe a system of LMT units.

Among the various systems of units, the former C.G.S. system is the best suited to the practices of biologists. However, it is easy to change from one system of units to another by the use of appropriate conversion factors.

In respect of the C.G.S. system, it is therefore necessary always to express a length in cm, a surface area in cm², a volume in cm³, a density in g.cm⁻³, a concentration in g.cm⁻³ or in mol.cm⁻³ and a time in seconds, which conditions are necessary in order to be able to obtain standardized models, the absence of which constitutes a deficiency in the biological sciences because of the absence of the use of units which are coherent between them (Hauton J.C. et al., Biochimie, 1987, 69, 177–204, *Lipid Biodynamics*: new perspectives). 1) Physical parameters of a well-defined spherical particulate species:

a spherical particle X, such as a lipogelosome (LGS), a gelosome (GS) or a hybrid structure between lipogelosomes (LGS) and gelosomes (GS) with a radius R in cm, is a polymolecular entity with a volume $v_X$ in cm³, a density $d_X$ in g.cm⁻³, a mass $m_X$ in g and a surface area $s_X$ in cm² (the physical parameters of a particle being expressed by lower-case characters).

Thus, one mole of X, i.e. N particles of X or $6.023 \times 10^{23}$ particles (the molar physical parameters being expressed by upper-case characters) has an XV (Molar Volume) $MV_X$ of $v_X N$ cm³, equal to $\frac{4}{3}\pi R^3 N$ cm³ or $25.22 \times 10^{23} R^3$ cm³, an MM (Molar Mass) $MM_X$ of $m_X N$ g or $25.22 \times R^3 d_X$ g and an MS (Molar Surface) $MS_X$ of $s_X N$ cm², equal to $4\pi R^2 N$ cm² or $75.68 \times 10^{23} R^2$ cm² ($\frac{4}{3}\pi = 4.188$, $\frac{4}{3}\pi N = 25.23 \times 10^{23}$, $4 = 12.5664$ and $4\pi N = 75.69 \times 10^{23}$).

If the concentration of the particulate species X is expressed in mol.cm⁻³ by [X], there then exists, per cm³ of a well-defined reference volume (aqueous phase, in vitro, total blood, plasma, interstitial fluid, bile, intraluminal contents, and the like), the following relationship giving the number $n_X$ of particles per cm³:

$$n_{X-}[X]N \text{ or } n_{X-}[X]/N^{-1}$$

(the inverse of Avogadro's number $N^{-1}$, equal to $0.166 \times 10^{-23}$, becomes a constant expressing in mol.cm⁻³ the concentration of a single atom, of a single molecule or of a single particle). A molar physical or chemical parameter of a particulate species, multiplied by N or divided by $N^{-1}$, gives the value of this parameter per particle.

2) Delipidation of unilamellar lipogelosomes (LGS):

In the case of unilamellar lipogelosomes (LGS) with a given radius R in cm, there exists an encapsulated, polymerized or non-polymerized, gelified aqueous phase, known as PP (Polar Phase), which exists in the form of a sphere with a radius (R–h) cm, h expressing the thickness in cm of the surface lipid bilayer, known as BIP (Bilayer Interfacial Phase). The encapsulated gelified aqueous sphere is denoted by the symbol GPC (Gelified Polar Core).

The results are obtained from the calculation method explained above and show the physical characteristics of unilamellar lipogelosomes (LGS) of various diameters and of microspheres in accordance with the invention, that is to say gelified microspheres obtained by delipidation (i.e. GPCs). The following symbols are used:

R=given radius of the lipogelosomes (LGS) in cm, h=thickness in cm of a surface lipid bilayer (BIP) which is in the region of $40 \times 10^{-8}$ cm (i.e. 40 Å or 4 nm). A half-BIP is therefore in the region of $20 \times 10^{-8}$ cm.

$MV_{LGS}$=molar volume in cm³ of lipogelosomes (LGS) with a given radius R.

$MV_{GPC}$=molar volume in cm³ of the gelified polar core (GPC) of unilamellar lipogelosomes (LGS) with a given radius R, i.e. the molar volume of the microspheres obtained by the delipidation of the unilamellar lipogelosomes (LGS).

$MV_{BIP}$=molar volume in cm³ of the sole surface BIP surrounding the unilamellar lipogelosomes (LGS) with a given radius R.

$MV_{BIP(o)}$=molar volume of the outer phospholipid monolayer of the sole surface BIP surrounding the unilamellar lipogelosomes (LGS) with a given radius R.

$MV_{BIP(i)}$=molar volume of the inner phospholipid monolayer of the sole surface BIP surrounding the unilamellar LGSs with a given radius R.

$MS_{LGS}$=molar surface in cm² of lipogelosomes (LGS) with a given radius R.

$MS_{GPC}$=molar surface in cm² of the GPCs with a radius (R–h) cm, i.e. the molar surface of the gelified microspheres obtained by delipidation.

Four examples are shown.

a) Unilamellar lipogelosomes (LGS) with R=100×10⁻⁸ cm (i.e. diameter of 20 nm):
  $MV_{LGS}$=2.55×10⁶ cm³
  $MV_{GPC}$=0.54×10⁶ cm³ (i.e. 22% of $MV_{LGS}$),
  $MV_{BIP}$=1.98×10⁶ cm³ (i.e. 78% of $MV_{LGS}$),
  $MV_{BIP(o)}$=1.23×10⁶ cm³ (i.e. 62.2% of $MV_{BIP}$),
  $MV_{BIP(i)}$=0.75×10⁶ cm³ (i.e. 37.8% of $MV_{BIP}$),
  $MS_{LGS}$=7.57×10¹² cm²,
  $MS_{GPC}$=2.72×10¹² cm².

b) Unilamellar lipogelosomes (LGS) with R=500×10⁻⁸ cm (i.e diameter of 100 nm):
  $MV_{LGS}$=315×10⁶ cm³,
  $MV_{GPC}$=247×10⁶ cm³ (i.e. 77.9% of $MV_{LGS}$),
  $MV_{BIP}$=70×10⁶ cm³ (i.e. 22.1% of $MV_{LGS}$),
  $MV_{BIP(o)}$=36×10⁶ cm³ (i.e. 52% of $MV_{BIP}$),
  $MV_{BIP(i)}$=33×10⁶ cm³ (i.e. 48% of $MV_{BIP}$),
  $MS_{LGS}$=189×10¹² cm²,
  $MS_{GPC}$=160×10¹² cm².

c) Unilamellar lipogelosomes (LGS) with R=2,500×10⁻⁸ cm (i.e. diameter of 500 nm):
  $MV_{LGS}$=39,413×10⁶ cm³,
  $MV_{GPC}$=37,545×10⁶ cm³ (i.e. 95.3% of $MV_{LGS}$),
  $MV_{BIP}$=1,862×10⁶ cm³ (i.e. 4.7% of $MV_{LGS}$),
  $MV_{BIP(o)}$=939×10⁶ cm³ (i.e. 50.4% of $MV_{BIP}$),
  $MV_{BIP(i)}$=923×10⁶ cm³ (i.e. 49.6% of $MV_{BIP}$),
  $MS_{LGS}$=4,730×10¹² cm²,
  $MS_{GPC}$=4,580×10¹² cm².

d) Unilamellar lipogelosomes (LGS) with R=10,000×10⁻⁸ cm (i.e. diameter of 2,000 nm or 2 microns):
  $MV_{LGS}$=2,522,432×10⁶ cm³,
  $MV_{GPC}$=2,492,284×10⁶ cm³ (i.e. 98.8% of $MV_{LGS}$),
  $MV_{BIP}$=30,155×10⁶ cm³ (i.e. 1.2% of $MV_{LGS}$),
  $MV_{BIP(o)}$=15,108×10⁶ cm³ (i.e. 50.1% of $MV_{BIP}$),
  $MV_{BIP(i)}$=15,047×10⁶ cm³ (i.e. 49.9% of $MV_{BIP}$),
  $MS_{LGS}$=75,690×10¹² cm²,
  $MS_{GPC}$=75,076×10¹² cm².

By delipidation of small unilamellar lipogelosomes (SULGS) or of large unilamellar lipogelosomes (LULGS), the sole surface lipid bilayer is extracted: only the GPCs (Gelified Polar Core) remain, thus giving polymerized homogeneous gelosomes (GS) (homogeneous polymerisomes) or non-polymerized homogeneous gelosomes (GS), as specified above.

Figure 5:
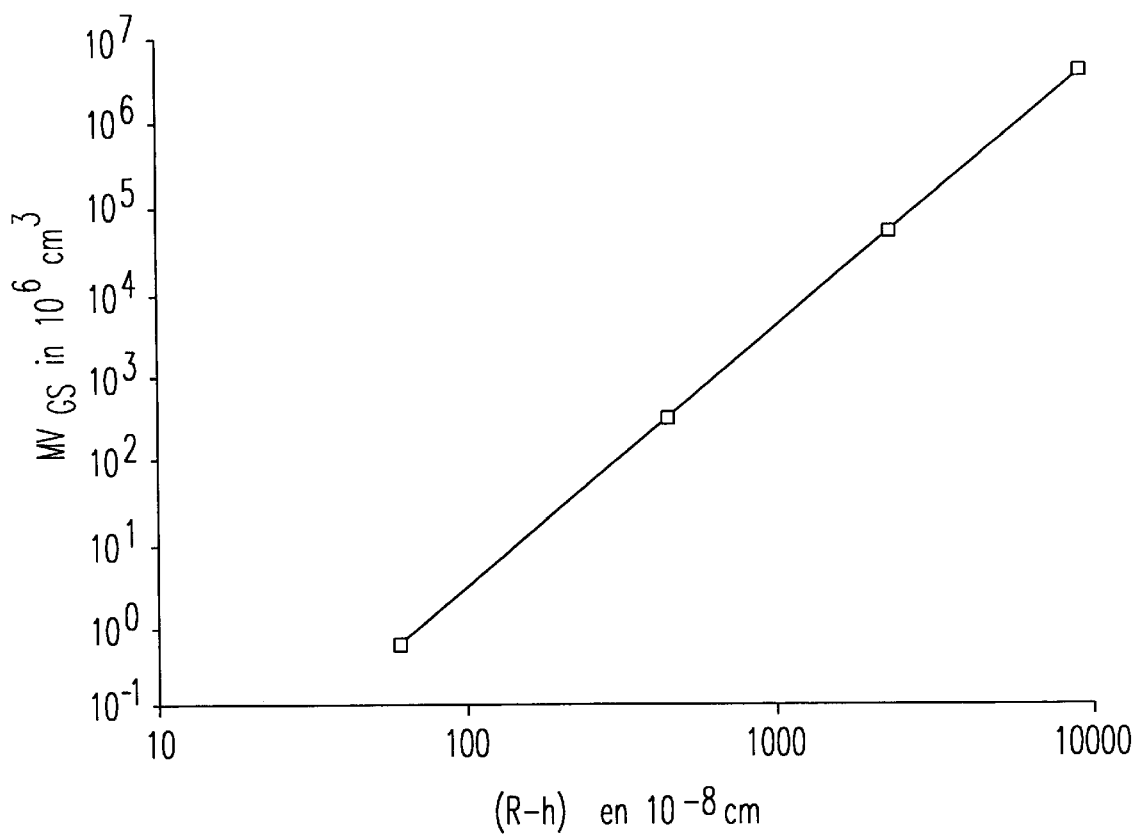
FIG. 5 illustrates the variations in the molar volumes of homogeneous gelosomes (SHGS or LHGS) as a function of the radius R-h (log/log coordinates)

FIGS. 4 and 5 show in log/log coordinates, on the one hand, the variations in the $MV_{LGS}$ values in cm³ as a function of the radius R, expressed in cm, and, on the other hand, those in the $MV_{GS}$ values as a function of the radius (R–h), expressed in cm.

The results, expressed as MV (Molar Volume) in cm³·mol⁻¹, can be expressed as MM (Molar Mass) in g·mol⁻¹ by multiplying the MV by the density d in g·cm⁻³. As the density $d_{pp}$ of the encapsulated, polymerized or non-polymerized, gelified aqueous polar phase and that of the surface lipid bilayer $d_{BIP}$ are known, it is then possible to calculate the density $d_{LGS}$ of the lipogelosomes (LGS) or that $d_{GS}$ of the gelosomes (GS).

3) Delipidation of multilamellar lipogelosomes (LGS):

The multilamellar lipogelosomes (LGS) (MLGS) consist of a polymerized or non-polymerized GPC (Gelified Polar Core) with a radius $R_{GPC}$, expressed in cm, on which are concentrically superimposed a first lipid bilayer with a thickness h in the region of 40×10⁻⁸ cm, then a polymerized or non-polymerized gelified aqueous layer with a thickness H of the order of 100×10–8 cm, then a second lipid bilayer, and so on.

As the symbol n represents the number of lipid bilayers, the radius R of a multilamellar lipogelosome (MLGS) is given by the equation (3) above.

Figure 6:
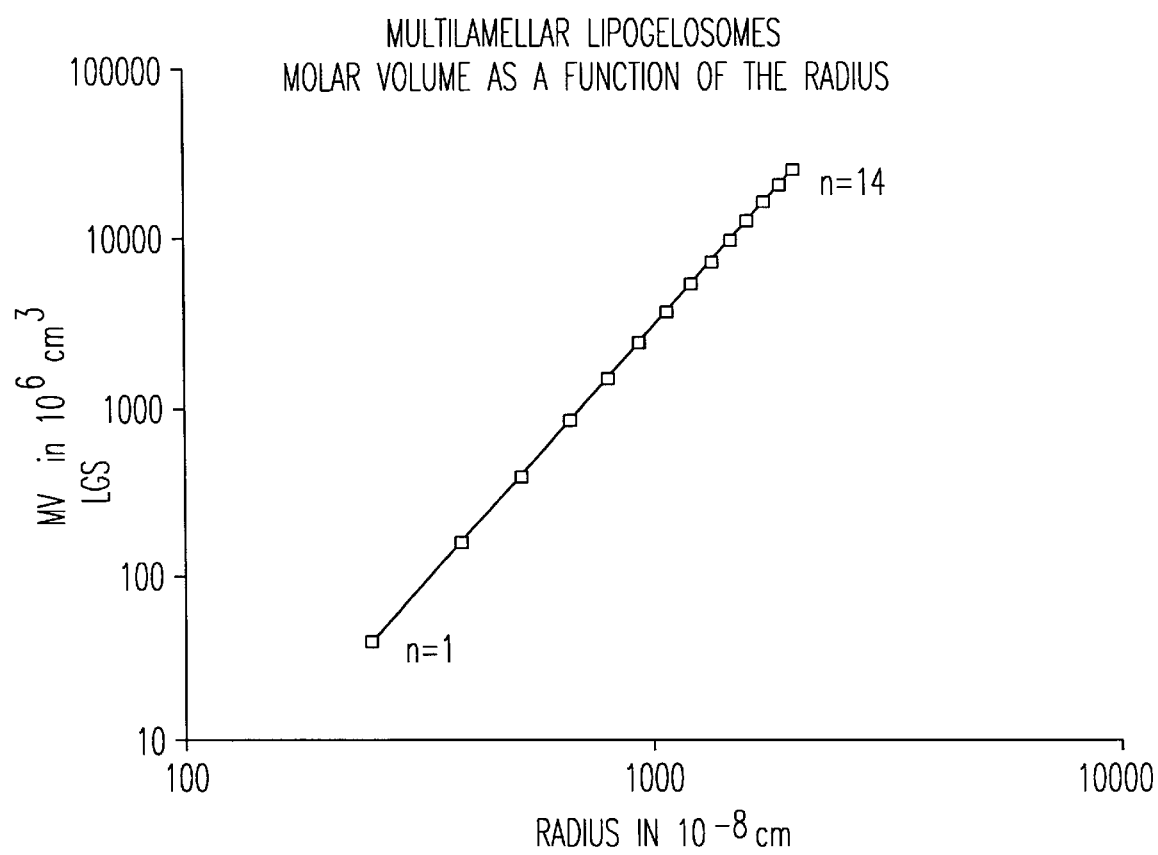
FIG. 6 illustrates the variations in the molar volumes of multilamellar lipogelosomes as a function of the radius R (log/log coordinates).

Table II shows, as an example, the variations in the $MV_{LGS}$ values and the respective volume percentages % $MV_{pp}$ of the encapsulated, polymerized or non-polymerized, gelified aqueous phase and % $MV_{BIP}$ of the lipid phase of an LGS having an $R_{GPC}$ of 210×10⁻⁸ cm and n lipid bilayers, and thus (n–1) polymerized or non-polymerized gelified aqueous layers, with a thickness 100×10⁻⁸ cm. FIG. 6 shows the abovementioned parameters, in log/log coordinates, for multilamellar lipogelosomes. In practice, it is necessary to determine the $RG_{GPC}$, n, h and H parameters of a defined species of multilamellar lipogelosome (MLGS) in order to fully specify their physical characteristics.

TABLE II

| BIP Number n | R 10⁻⁸ cm | $MV_{LGS}$ 10⁶ cm³·mol⁻¹ | % $MV_{pp}$ | % $MV_{BIP}$ |
|---|---|---|---|---|
| 1 | 250 | 39 | 59.3 | 40.7 |
| 2 | 390 | 150 | 61.8 | 38.2 |
| 3 | 530 | 370 | 63.7 | 36.8 |
| 4 | 670 | 760 | 65.2 | 34.8 |
| 5 | 810 | 1,340 | 66.2 | 33.8 |
| 6 | 950 | 2,160 | 67 | 33.0 |
| 7 | 1,090 | 3,270 | 67.5 | 32.5 |
| 8 | 1,230 | 4,690 | 68 | 32.0 |
| 9 | 1,370 | 6,480 | 68.3 | 31.7 |
| 10 | 1,510 | 8,680 | 68.6 | 41.4 |
| 11 | 1,650 | 11,300 | 68.8 | 31.2 |
| 12 | 1,790 | 14,500 | 69.0 | 31.0 |
| 13 | 1,930 | 18,100 | 69.2 | 30.8 |
| 14 | 2,070 | 22,400 | 69.3 | 30.7 |

In accordance with the invention, during surface delipidation, only the surface or outer lipid bilayer with a thickness h of the multilamellar lipogelosomes (MLGS) is extracted. Hybrid structures between lipogelosomes (LGS) and gelosomes (GS) are then obtained comprising a polymerized or non-polymerized gelified aqueous layer with a thickness H and containing (n–1) lipid bilayers surrounding the polymerized or non-polymerized GPC. The radius of these hybrid structures will be equal to $R_{LGS}$–h, $R_{LGS}$ being the radius of the multilamellar lipogelosomes (MLGS) before delipidation.

In accordance with the invention, during complete delipidation, all the lipid bilayers of the multilamellar lipogelosomes (MLGS) are extracted, leaving a space which will be occupied by the aqueous polar phase in the liquid state during organic phase/aqueous phase partition. Non-homogeneous structures, denoted as multilayered gelosomes (MGS), are thus obtained, the starting encapsulated gelified aqueous phase of which, originating from the multilamellar lipogelosomes (MLGS), may be polymerized (multilayered polymerisomes) or may be non-polymerized. The radius of these non-homogeneous gelosomes (GS) will be equal to $R_{LGS}$–h, $R_{LGS}$ being the radius of the multilamellar lipogelosomes (MLGS) before delipidation. After complete delipidation, the molar percentage of the lipid space thus released and occupied by the liquid aqueous phase originating from the solvent/water partition will be equal to the % $MV_{BIP}$ of the non-delipidated multilamellar lipogelosomes (MLGS).

EXAMPLE 2

Preparation of microspheres in accordance with the invention.

A. Products:

a) Phospholipids:

The lipid phase is composed of deoiled soya phospholipids from Stern-France, presented in the dry form, and is used at a concentration of 7.5% by weight/volume.

b) Non-polymerizable gelifiable agents:

gelatin, of B150 Blooms type from Sanofi-Bioindustries, France; it has a melting temperature between 30 and 35° C. and is used at a concentration of 7.5% by weight/volume.

carragheenin from Sanofi-Bioindustries, France. The 80/20 (w/w) gelatin/carragheenin mixture has a melting temperature of 50° C. This mixture is used at a concentration of 7.5% by weight/volume.

The gelatin or the gelatin/carragheenin mixture, in the abovementioned proportions and concentrations, gives a non-polymerized gelified aqueous phase below the respective melting temperatures of 30–35° C. and 50° C.

C) Polymerizable gelifiable agent:

Acrylamide/bis-acrylamide from Sigma.

A polymerized gelified aqueous phase is obtained by mixing acrylamide/bis-acrylamide from Sigma, Temed from Blo-Rad and ammonium persulphate from Bio-Rad under appropriate concentration conditions; a concentration of 15% by weight/volume of acrylamide/bis-acrylamide is used in particular.

The polyacrylamide gel is a non-limiting example selected from the polymerizable compounds.

d) Cryoprotective agent:

sucrose from Sigma (used at 7.5% by weight/volume).

B. Procedure:

The concentrations given are those used in the starting aqueous phase, in which the phospholipids are dispersed.

The following process is preferable, among the various processes used for the preparation of liposomes and lipogelosomes and which are suitable on an industrial scale, because it contains an ultrasonication stage (suitable on an industrial scale) which makes it possible to obtain a large majority of lipogelosomes (LGS) with a diameter of the order of 100 nm, i.e. a radius R of $500 \times 10^{-8}$ cm. By quasi-elastic scattering, measured with a laser particle sizer from Sema-Tech (Nice), 81% by number of a population of lipogelosomes (LGS) are centered on a diameter of 92.7 nm (a radius R of $413 \times 10^{-8}$ cm) and 19% on a diameter of 312 nm (a radius R of $1,560 \times 10^{-8}$ cm).

This process comprises:

1) Slow mechanical stirring of deoiled soya phospholipids from Stern-France at a concentration of 7.5% (w/v) for 3 hours, dispersed in an aqueous phase containing the gelifying agent (7.5% of gelatin or of the gelatin/carragheenin mixture or 15% of acrylamide/bis-acrylamide without Temed® and ammonium persulphate), in the liquid state. 7.5% (w/v) sucrose is optionally added as cryoprotective agent.

a) For the non-polymerizable gelifying agents (gelatin or gelatin/carragheenin mixture), this mechanical stirring stage is carried out above the melting point of these gelifying agents.

b) For polyacrylamide as polymerizable gelifying agent, this mechanical stirring is carried out without addition of Temed® and of ammonium persulphate, which prevents the polymerization process.

This mechanical stirring stage produces multilamellar liposomes (since not yet converted to lipogelosomes) with a diameter varying from 297 to 2,084 nm with a mean diameter of 504 nm (i.e. a radius R of $2,520 \times 10^{-8}$ cm).

2) Ultrasonication by a Sonroreator ultrasound generator (Undatim Ultrasonics, Louvain-La-Neuve, Belgium) with titanium sonotrodes suited to the volume of the liposome suspension. A frequency of 20 kHz is used, the power being suited to the volume of the liposome suspension. For volumes of the order of 10 $cm^3$, the sonication time is between 3 and 4 minutes whereas it is raised to 10 minutes for volumes of 700 to 750 $cm^3$.

a) For the abovementioned non-polymerizable gelifying agents, the sonication is carried out above the melting point of these agents.

b) For the polyacrylamide polymerizable gelifying agent, Temed® and ammonium persulphate, which induce the polymerization process, are added at the beginning of the ultrasonication. Immediate aqueous dilution at the end of sonication (1/10 to 1/20th) prevents the polymerization of the aqueous phase which is not encapsulated in the liposomes, whereas the aqueous phase encapsulated in the latter will polymerize.

3) Removal of the non-encapsulated compounds by tangential ultrafiltration, the liposomes and/or lipogelosomes remaining in the retentate. The equipment used, sourced from Filtron (France), can be adjusted as a function of the volume to be treated. The membranes used have a cut-off threshold of 300 kDa or 1,000 kDa (i.e., more correctly, of 300,000 or 1 million $g.mol^{-1}$).

In the absence of aqueous dilution, the tangential ultrafiltration of the liposomes has to be carried out at a temperature greater than the melting temperature of the non-polymerizable gelifying agents (gelatin or gelatin/carragheenin mixture). Appropriate aqueous dilution after the sonication can enable the tangential ultrafiltration to be used at room temperature. Papain has been used to fragment the non-encapsulated gelatin in order to increase the yield of the dialysis of the non-polymerizable encapsulated gelified compounds. Subsequently, lowering the temperature will convert the liposomes to lipogelosomes which will be concentrated in the retentate.

For polyacrylamide as polymerizable gelifying agent, appropriate dilution and ultrafiltration imediately following the sonication removes the non-encapsulated polymerizable agent, whereas the encapsulated polymerizable agent will convert the liposomes to lipogelosomes.

4) Surface or complete delipidation of the lipogelosomes (LGS):

The lipogelosomes (LGS), more or less concentrated in the ultrafiltration retentate, according to the operating conditions chosen, are surface-delipidated by a water-immiscible solvent (or a mixture of water-immiscible solvents). Heptane has been used as water-immiscible solvent. Complete delipidation is obtained by using a water-miscible solvent, or preferably partially water-miscible solvent, such as n-butanol. After a two-phase organic phase/aqueous phase partition, the various microspheres described above are recovered in the polar aqueous phase, i.e.: non-polymerized small homogeneous gelosomes (SHGS) or large homogeneous gelosomes (LHGS), polymerized small homogeneous gelosomes (SHGS) or large homogeneous gelosomes (LHGS) (or homogeneous polymerisomes), multilamellar lipogelosomes (MLGS) surrounded by a non-polymerized gelified aqueous layer (hybrid structures between lipogelosomes (LGS) and gelosomes (GS)), multilamellar lipogelosomes (MLGS) surrounded by a polymerized gelified aqueous layer (hybrid structures between lipogelosomes (LGS) and gelosomes (GS)), and non-polymerized multilayered gelosomes or polymerized multilayered gelosomes (multilayered polymerisomes).

Monitoring the decrease in the diameters obtained by surface or complete delipidation of the unilamellar lipogelosomes (LGS), by laser particle size determination and electron microscopy, makes it possible to confirm that the process used has been carried out correctly. Moreover, the quantitative determination of the lipids in the organic phase obtained after the solvent(s) /water partition makes it possible to confirm the efficiency of the delipidation.

As emerges from the above, the invention is in no way limited to those of its implementation, production and application methods which have just been described more explicitly; on the contrary, it encompasses all the variations thereof which can come to the mind of an expert in the subject, without departing from the context or from the scope of the present invention.

What is claimed is:

1. Microspheres comprising a gelified polar core around which are superimposed one lipid bilayer and one gelified polar layer, and wherein the outermost layer is a polymerized or non-polymerized gelified layer, said microspheres being prepared by the method of:
   preparing multilamellar liposomes having two lipid bilayers and a gelified polar core;
   thereafter removing the surface lipid bilayer of said multilamellar liposomes with a water-immiscible organic solvent or a mixture of water-immiscible organic solvents;
   thereafter two-phase partitioning the organic phase and the aqueous phase; and
   thereafter separating the aqueous phase containing the micropheres with an outermost polymerized or non-polymerized gelified layer.

2. Microspheres according to claim 1, wherein the microspheres have a diameter of between 20 and 600 nm.

3. Microspheres of claim 1, wherein the gelified substance is selected from the group consisting of polymerized and non-polymerized gelified compounds.

4. Microspheres of claim 3, wherein the non-polymerized gelified substance is selected from the group consisting of gelatin, agarose and carragheenins and the polymerized gelified substance is a polyacrylamide.

5. Microspheres of claim 3, wherein the non-polymerized gelified compounds are selected from the group consisting of polysaccharides and polypeptides.

6. Microspheres comprising a gelified polar core around which are superimposed one aqueous layer in the liquid state and one gelified polar layer, and wherein the outermost layer is a polymerized or non-polymerized gelified layer, said microspheres being prepared by the method of:
   preparing multilamellar liposomes having a gelified polar core;
   thereafter removing all the lipid bilayers of said multilamellar liposomes with a water-miscible or partially water-miscible organic solvent or a mixture of water-miscible or partially water-miscible organic solvents;
   thereafter two-phase partitioning the organic phase and the aqueous phase;
   thereafter separating the organic solvent or solvents from the aqueous phase; and
   thereafter separating the microspheres with an outermost polymerized or non-polymerized gelified layer.

7. Microspheres of claim 6, wherein the microspheres have a diameter of between 20 and 600 nm.

8. Microspheres of claim 6, wherein the gelified substance is selected from the group consisting of polymerized and non-polymerized gelified compounds.

9. Microspheres of claim 8, wherein the non-polymerized gelified substance is selected from the group consisting of gelatin, agarose and carragheenins and the polymerized gelified substance is polyacrylamide.

10. Microspheres of claim 8, wherein the non-polymerized gelified compounds are selected from the group consisting of polysaccharides and polypeptides.

11. Microspheres of claim 6, wherein, when a water-miscible organic phase is used, a non-polar organic solvent is added prior to the two-phase partitioning.

12. Method for the preparation of microspheres comprising a gelified polar core around which are superimposed one lipid bilayer and one gelified polar layer, and wherein the outermost layer is a polymerized or non-polymerized gelified layer, which method comprises:
   preparing multilamellar liposomes with a gelified polar core and two lipid bilayers;
   removing the surface lipid bilayer of the said multilamellar liposomes with a water-immiscible organic solvent or a mixture of water-immiscible organic solvents;
   thereafter two-phase partitioning the organic phase and aqueous phase; and
   thereafter separating the aqueous phase containing the microspheres with an outermost polymerized or non-polymerized gelified layer.

13. Method for the preparation of microspheres comprising a gelified polar core around which are superimposed one aqueous layer in the liquid state and one gelified polar layer, and wherein the outermost layer is a polymerized or non-polymerized gelified layer, which method comprises:
   preparing multilamellar liposomes with a gelified polar core;
   thereafter removing all the lipid bilayers of the said multilamellar liposomes with a water-miscible or partially water-miscible organic solvent or a mixture of water-miscible or partially water-miscible organic solvents;
   thereafter two-phase partitioning the organic phase and the aqueous phase;
   thereafter separating the organic solvent or solvents from the aqueous phase; and
   thereafter separating the microspheres with an outermost polymerized or non-polymerized gelified layer.

14. A composition comprising the microspheres of claim 1, and an active substance.

15. The compositon of claim 14, wherein said active substance is a medicament.

16. The composition of claim 14, wherein said active substance is a macromolecule.

17. The composition of claim 14, wherein said active substance is a diagnostic reagent.

18. A composition comprising the micropheres of claim 6, and an active substance.

19. The composition of claim 18, wherein said active substance is a medicament.

20. The composition of claim 18, wherein said active substance is a macromolecule.

21. The composition of claim 18, wherein said active substance is a diagnostic reagent.

* * * * *

UNITED STATES PATENT AND TRADEMARK OFFICE
CERTIFICATE OF CORRECTION

PATENT NO.   : 6,221,387 B1  
DATED        : April 24, 2001  
INVENTOR(S)  : Jacques Hauton et al.

It is certified that error appears in the above-identified patent and that said Letters Patent is hereby corrected as shown below:

Column 13,
Line 35, "micropheres" should read -- microspheres --.

Column 14,
Line 58, "micropheres" should read -- microspheres --.

Signed and Sealed this

Fourth Day of December, 2001

Attest:

NICHOLAS P. GODICI

*Attesting Officer*  *Acting Director of the United States Patent and Trademark Office*